United States Patent
O'Donnell et al.

(10) Patent No.: US 7,204,592 B2
(45) Date of Patent: Apr. 17, 2007

(54) STEREOSCOPIC IMAGE PROJECTION SYSTEM

(75) Inventors: Eugene Murphy O'Donnell, Fishers, IN (US); Brent William Hoffman, Mooresville, IN (US); Estill Thone Hall, Jr., Fishers, IN (US); Valter Drazic, Betton (FR)

(73) Assignee: Thomson Licensing, Boulogne-Billancourt (FR)

( * ) Notice: Subject to any disclaimer, the term of this patent is extended or adjusted under 35 U.S.C. 154(b) by 103 days.

(21) Appl. No.: 10/502,722

(22) PCT Filed: Jan. 27, 2003

(86) PCT No.: PCT/US03/02244

§ 371 (c)(1),
(2), (4) Date: Jul. 27, 2004

(87) PCT Pub. No.: WO03/065737

PCT Pub. Date: Aug. 7, 2003

(65) Prior Publication Data

US 2005/0017938 A1 Jan. 27, 2005

(30) Foreign Application Priority Data

Jan. 28, 2002 (FR) .................... 02 001865

(51) Int. Cl.
*G03B 21/00* (2006.01)
*H04N 15/00* (2006.01)
*G02B 27/26* (2006.01)

(52) U.S. Cl. .................... 353/7; 353/20; 348/51; 359/465

(58) Field of Classification Search .................... 353/7, 353/8, 20, 33, 10, 81; 349/15, 9, 465, 464; 348/51, 52, 54, 58
See application file for complete search history.

(56) References Cited

U.S. PATENT DOCUMENTS 5,784,038 A 7/1998 Irwin (Continued)

FOREIGN PATENT DOCUMENTS

EP 1081964 3/2001

OTHER PUBLICATIONS

Patent Abstracts of Japan, vol. 2000, No. 23, Feb. 10, 2001 and JP 2001-174775.

(Continued)

*Primary Examiner*—W. B. Perkey
*Assistant Examiner*—Andrew Sever
(74) *Attorney, Agent, or Firm*—Joseph J. Laks; Harvey D. Fried; Patricia Verlangieri

(57) ABSTRACT

A liquid crystal display projection system for pictures that can be viewed stereoscopically, comprising: a source of a repetitive three color sequence of light; first and second imagers responsive to respective drive signals representative of the same picture from different angles of view; at least a first polarizing beam splitter for separating said repetitive three-color sequence of light into a P polarized three color sequence of light and an S polarized three color sequence of light, said S polarized three color sequence of light illuminating said first imager and said P polarized three color sequence of light illuminating said second imager; a first filter for removing P polarized light directed to said first imager; and, a second filter for removing P polarized light reflected from said second imager, wherein said light reflected from said first imager and said light filtered by said second filter form a stereoscopic image when viewed through respective P and S polarizing lenses.

8 Claims, 3 Drawing Sheets

U.S. PATENT DOCUMENTS

| | | | |
|---|---|---|---|
| 5,833,338 A | 11/1998 | Barak | |
| 5,921,650 A | 7/1999 | Doany et al. | |
| 6,309,071 B1 * | 10/2001 | Huang et al. | 353/31 |
| 2003/0020809 A1 * | 1/2003 | Gibbon et al. | 348/51 |
| 2004/0114234 A1 * | 6/2004 | Sedlmayr | 359/485 |

OTHER PUBLICATIONS

Copy of PCT Search Report Dated Jul. 16, 2003.

Copy of EP Search Report Dated Jun. 16, 2002.

* cited by examiner

STEREOSCOPIC IMAGE PROJECTION SYSTEM

This application claims the benefit, under 35 U.S.C.§365 of International Application PCT/US03/02244, filed Jan. 27, 2003, which was published in accordance with PCT Article 21(2) on Aug. 7, 2003 in English and which claims the benefit of European patent application No. 02001865.1, filed Jan. 28, 2002.

This invention relates to the field of light engines for projection systems, and more particularly, to a light engine architecture that enables stereoscopic viewing.

The existing technology in projection systems is inefficient, requiring major optical systems to transform the light into a usable form. Arc lamps and other similar light sources are by their nature broadband in output and therefore generate infrared, ultraviolet, and non-primary visible light, as well as the red, green, and blue light which is useful for projection. The inefficiencies of color filters used to process this light also leads to broader band colors and therefore smaller color space. Light sources such as arc lamps also produce random "mixed" polarization, and therefore require additional optical system components to handle polarization separation. To further enhance "étendue", a complex system of integrators and collimators are required to transform a focused beam from a light source (such as an arc lamp) into a uniform rectangular illumination. Étendue is generally known as the product of radiant flux density and the area of a radiating or receiving surface. This is used to determine absolute values for the emitted (reflected or transmitted) energy, in order to control the overall energy balance. In addition, since light coming from the lamps is essentially white, dedicated dichroic filters would be necessary to produce red, green, and blue light necessary for a projection system. As a result of all the hardware required to overcome the problems described above, a large, bulky optical system would be needed for the purpose of achieving adequate through-put of light through a typical light engine. Even with all the existing schemes to increase the throughput of light through a light engine, the best systems achieve between 40–60% throughput. Many existing systems use a single LCOS panel for each color, and attempt to maximize the illumination with the appropriate polarization using polarization recovery systems, such as PBS arrays and other expensive or inefficient schemes. Thus, a need exists for a light engine which substantially increases system throughput in terms of light while adding minimal cost.

Other systems utilize more than one imager or panel for each color, requiring at least four imagers. Three of the imagers must be aligned with the fourth imager. Each of the three imagers must be aligned with respect to six degrees of movement. This is extraordinarily difficult, not only because the pixel size is on the order of only 10 microns, and each respective pixel of each imager must be aligned perfectly to enable sharp pictures, but each imager is subject to thermal stress and movement as the light engine heats up. Thus, a further need exists for a light engine that not only can substantially increase system through put, but is much less complex and much less expensive to build, align and operate.

It should also be noted that existing stereoscopic displays typically require special glasses for viewing the stereo image. Several techniques have been around including using Red and green to separate left and right eye images of a monochrome picture. This should work if you have a red/green viewer. Another technique is frame sequential left and right eye images with glasses that incorporate LCD shutters that switch in synchronism with the image. The glasses are active and so require power and control circuitry, and a timing signal from the display. Another technique involves polarization to separate the left and right eye images. This is the technique used in the cinema. Its use with electronic displays is less prevalent but can be implemented using an electrically switchable polarizer in front of the display and frame sequential images. The implementation would be comparable to the LCD where a filter would be used to obtain color in frame sequential CRT displays. The latter two approaches require frame sequential left and right images. It is essential that no residual image from one eye remains on the display when the image is switched to the other. Thus with present technology they can only be implemented with fast CRT displays. Thus, a further need exists for a method of viewing a stereoscopic image using polarization that would not require specialized lenses.

In a first aspect of the present invention, a device for generating a stereoscopic image using a liquid crystal display projection system comprises at least a first imager and a second imager and at least a first polarizing beam splitter for substantially separating P polarized light from S polarized light and directing the P polarized light to the first imager and the S polarized light to the second imager. The system further comprises a first filter for filtering out a substantial portion of any P polarized light reflected from the first imager and a second filter for filtering out a substantial portion of any P polarized light in the S polarized light split out by the at least first polarizing beam splitter.

In a second aspect of the present invention, a light engine arrangement for generating a stereoscopic image comprises at least a first imager and a second imager and a means of substantially separating P polarized light from S polarized light and directing the P polarized light to the first imager and the S polarized light to the second imager. The light engine arrangement further comprises a first filter for filtering out a substantial portion of any P polarized light reflected from the first imager and a second filter for filtering out a substantial portion of any P polarized light in the S polarized light split out by the means of substantially separating.

In a third aspect of the present invention, a method of viewing a stereoscopic image using polarization comprises the steps of driving a first imager with a first image signal modulated for S polarization and driving a second imager with a second image signal modulated for P polarization, wherein the first image signal and the second image signal combined provide a stereoscopic view for projection by a projection lens. The method further comprises the steps of injecting unpolarized light into the system and separating P polarized light from S polarized light from the injected unpolarized light. Additionally, the method further comprises the steps of directing the P polarized light to the first imager and directing S polarized light reflected from the first imager toward the projection lens after filtering the reflected S polarized light for stray P polarized light and directing the S polarized light toward the second imager after filtering the S polarized light for stray P polarized light and directing reflected P polarized light reflected from the second imager toward the projection lens.

Figure 1:
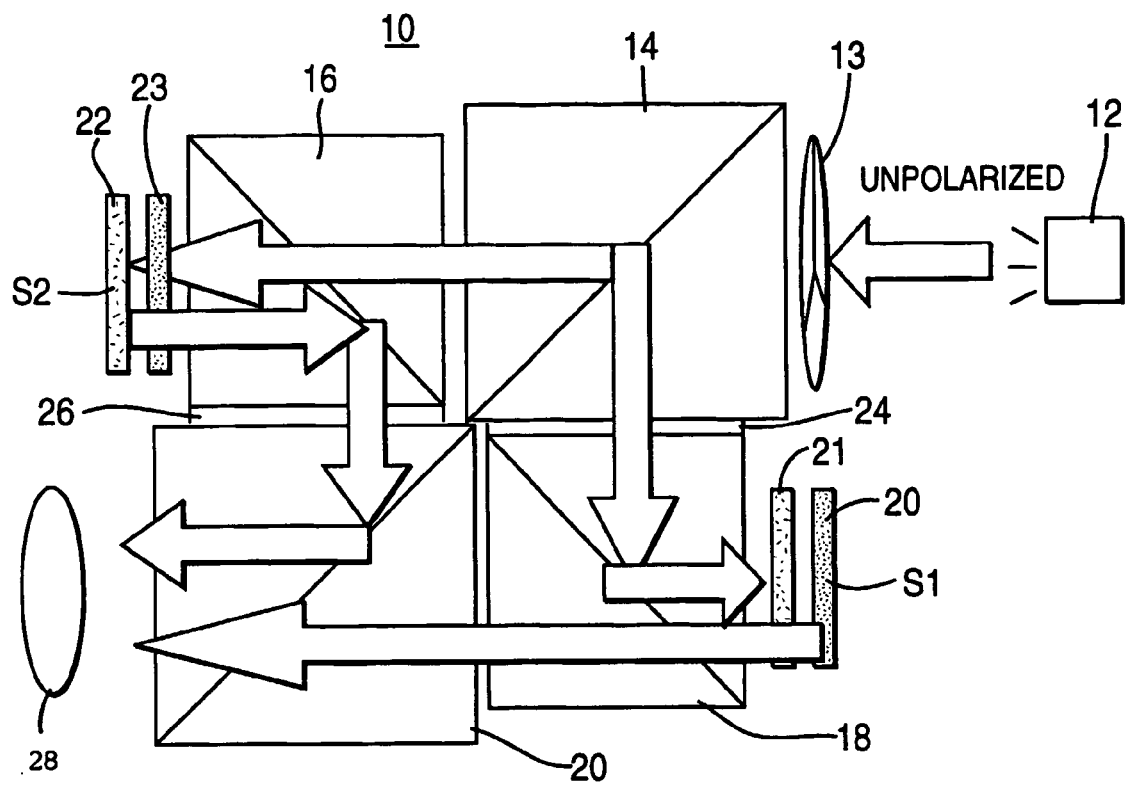
FIG. 1 is a block diagram of a light engine architecture in accordance with the present invention.

Referring to FIG. 1, a novel architecture 10 for generating a stereoscopic image using polarization with a light engine is shown. The architecture disclosed further significantly increases system throughput in terms of light brightness. While existing systems attempt to increase throughput using a single panel or imager, the present invention utilizes at least a second panel or imager. Adding a second panel to the system, and using a color wheel as is done with Digital Micromirror Device (DMD)-type systems effectively doubles the total luminous flux. Unpolarized light is injected into the system. P polarized light is separated from S polarized light at the first PBS, wherein P polarized light goes to one imager and S polarized light goes to another one. Hence there is a polarization recovery operated by the addition of one imager or panel. The cost penalty is that the additional panel is needed, and a method of achieving proper alignment of the two separate imagers is required. The cost of an additional imager is well offset by the overall savings in cost. The two panels can be driven with the same signal to enhance system throughput, for example doubling the light output. Alternatively, the two imagers can be driven by two different signals to obtain the stereoscopic effect previously mentioned.

Such a system achieves the advantages of reducing complexity and cost because the invention can be embodied with only two imagers, and can provide almost as much light through put as systems having four or more imagers.

A liquid crystal display projection system, architecture or system 10 comprises at least a first imager 22 and a second imager 20. Preferably, these imagers are liquid crystal on silicon (LCOS) display devices. The system 10 can further comprise at least a first polarizing beam splitter 14 for substantially separating P polarized light from S polarized light and directing the P polarized light to the first imager 22 and the S polarized light to the second imager 20. Additionally, the system comprises a first filter 26 for filtering out a substantial portion of any P polarized light reflected from the first imager 22 and a second filter 24 for filtering out a substantial portion of any P polarized light in the S polarized light split out by the at least first polarizing beam splitter 14. Preferably, the system includes four PBSs including the first PBS 14, a second PBS 18 for directing S polarized light split from the first PBS toward the second imager, a third PBS 16 for directing S polarized light reflected from the first imager towards a fourth PBS 20, wherein the fourth PBS 20 directs S polarized light reflected from the first imager and P polarized light from the second imager towards a projection lens 28. In such a system, the liquid crystal display projection system 10 would further preferably include a first quarter wave plate 23 between the third PBS 16 and the first imager 22 and a second quarter wave plate 21 between the second PBS 18 and the second imager 21. It should be understood that the use of quarter wave plate could be obviated in a system using a wire grid polarizer as will be further discussed below. The system further comprises a source of unpolarized light 12 such as an arc lamp and rotatable color wheel 13 placed between at least the first PBS and the source of unpolarized light. The lamp and color wheel are a means for supplying a repetitive sequence of colored light, for example red, green, blue, red, green, blue and so on. The rotating wheel and corresponding drive signals supplied to the imagers are synchronized as is known in the art.

One basic advantage of the system of the present invention is that even if the étendue is increased by the polarization splitting, it does not end up in a loss of brightness as a second imager is used to increase the system's étendue and match it to that of the illumination when signals S1 and S2 are the same drive signal. Alternatively, signals S1 and S2 can be different in order to produce a polarization based stereo vision experience. In the stereoscopic embodiment, the user needs only polarizing glasses, not LCD shutters. This dual panel system would require added mechanical complexity and alignment for the second panel and the corresponding drivers for the panels.

Referring again to FIG. 1, the first filter 26 and second filter 24 advantageously and substantially increase image contrast, a significant problem in the prior art because there can not be an analyzer at the output just before the lens or a clean up polarizer at the input. The first and second filters serve as clean up polarizers in each channel. The role of these clean up polarizers are discussed further on a numerical example in the alternative embodiment discussed below regarding wire grid PBSs instead of glass PBS. It should be understood within contemplation of the present invention that additional filters could be used. For example, additional filters (not shown) between the interface of PBS 14 and PBS 16 and between the interface of PBS 18 and PBS 20 could even further improve contrast as well and clean up the illumination from further unwanted polarization. These filters could be dye type or wire grid polarizers. It should also be noted that filters or polarizers set in the light reflected off the imagers act as analyzers that are used to clean up residual polarization from the imagers (see filter 26 or a filter (not shown) located between PBS 18 and PBS 20). Since imagers are imperfect and could reflect back elliptical polarized light instead of linear light, the additional filters described herein would be suitable when the PBSs in the imaging path of the light do not clean enough of the residual polarization.

Figure 2:
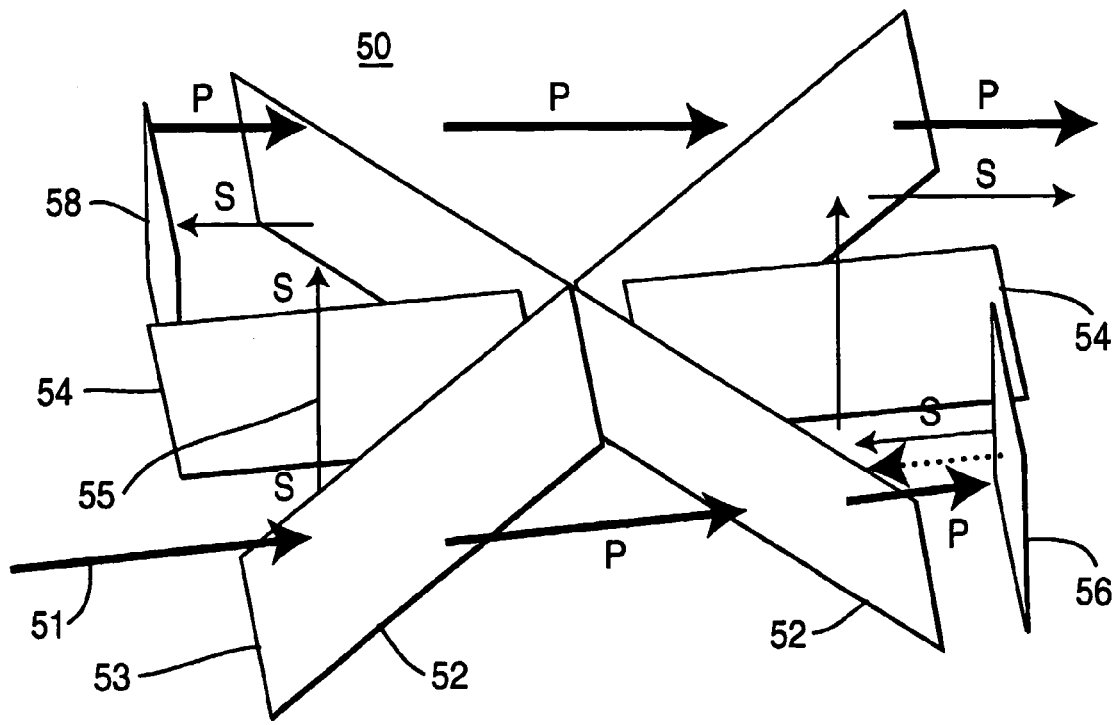
FIG. 2 is another block diagram of a light engine architecture using Wire Grid Polarizer in accordance with the present invention.

Referring to FIG. 2, the light engine arrangement or system 50 can be made out of wire grid polarizers (WGPs) made by the company Moxtek. A WGP is constructed by forming a series of closely-spaced aluminum bars on a glass substrate. In other words, a WGP is constructed of a thin layer of aluminum wires on a glass substrate that makes for an exceptional PBS. As with PBSs, this grid reflects light of one polarization state while transmitting light of the orthogonal polarization state. This reflective property coupled with the WGP's rugged construction enables many new uses in projection systems. WGPs are less expensive than glass PBSs. The WGP as shown can be constructed in sheet format or sandwiched between other components. For a wire grid PBS, the typical transmission of P-polarized light is of 85% (blue channel, incidence angle of 45 degrees), so that 15% of P-polarized light is reflected off the PBS. The system 50 includes the wire grid polarizer 52 and a first imager 56 in a direct path for the illumination where arrow 51 represents the unpolarized light provided as an input into system 50. A second imager 58 receives illumination on an all-reflected path. For the direct path, $0.85^2=0.7225$ of the P polarized light from the input illumination reaches the first imager 56. In a black state, the first imager ideally all that light, and on the output, it bounces twice on the WGP 52 before going out of the system. Hence, the black state light throughput is $0.85^2 \times 0.15^2$. For a white state, the first imager 56 is rotating the polarization to S, and then as the typical reflection coefficient for S is of 0.0033, the white state light throughput is $0.85^2 \times 0.99672$, so that the contrast is finally $0.9967^2/0.15^2 = 44:1$, where contrast is determined by dividing the white state light throughput by the black state light throughput. Unfortunately, contrast ratio is extremely low. A similar calculation gives exactly the same result for the other channel. The main contributor to the low contrast is the P reflected light on both wire grid PBSs represented by the dashed arrows.

The present invention enhances the contrast by canceling the two reflected P polarization states in both channels by adding clean up polarizers or filters 54. Dye polarizers could be used if the irradiance on their surface does not destroy them, but preferably wire grid polarizers are used such as the Proflux brand WGP. Preferably, a high transmission WGP can be oriented so that it just transmits 0.10% of P light and could be placed after the first reflection of P polarized light in both channels. In this case, the black level falls down to $0.85^2 \times 0.15^2 \times 0.001$, and the white state to $0.85^2 \times 0.9967^2 \times 0.835$, where 0.835 is the typical transmission of the high transmission wire grid polarizer for the white state polarization. The contrast in this case is above 35000:1. Thus, without the clean up polarizers or filters 54, loss of contrast will result due to a high residual reflection of P-polarized light in the black state. With the clean up polarizers, the contrast can be boosted by a factor of 500–1000. The use of WGPs in the embodiment of FIG. 2 also obviates the need to use quarter wave plates as was used in the embodiment of FIG. 1 where conventional glass PBSs were used. It should also be noted that the grids having wires 53 and 55 on the WGPs 52 and 54 respectively should preferably be oriented as shown in FIG. 2.

Figure 3:
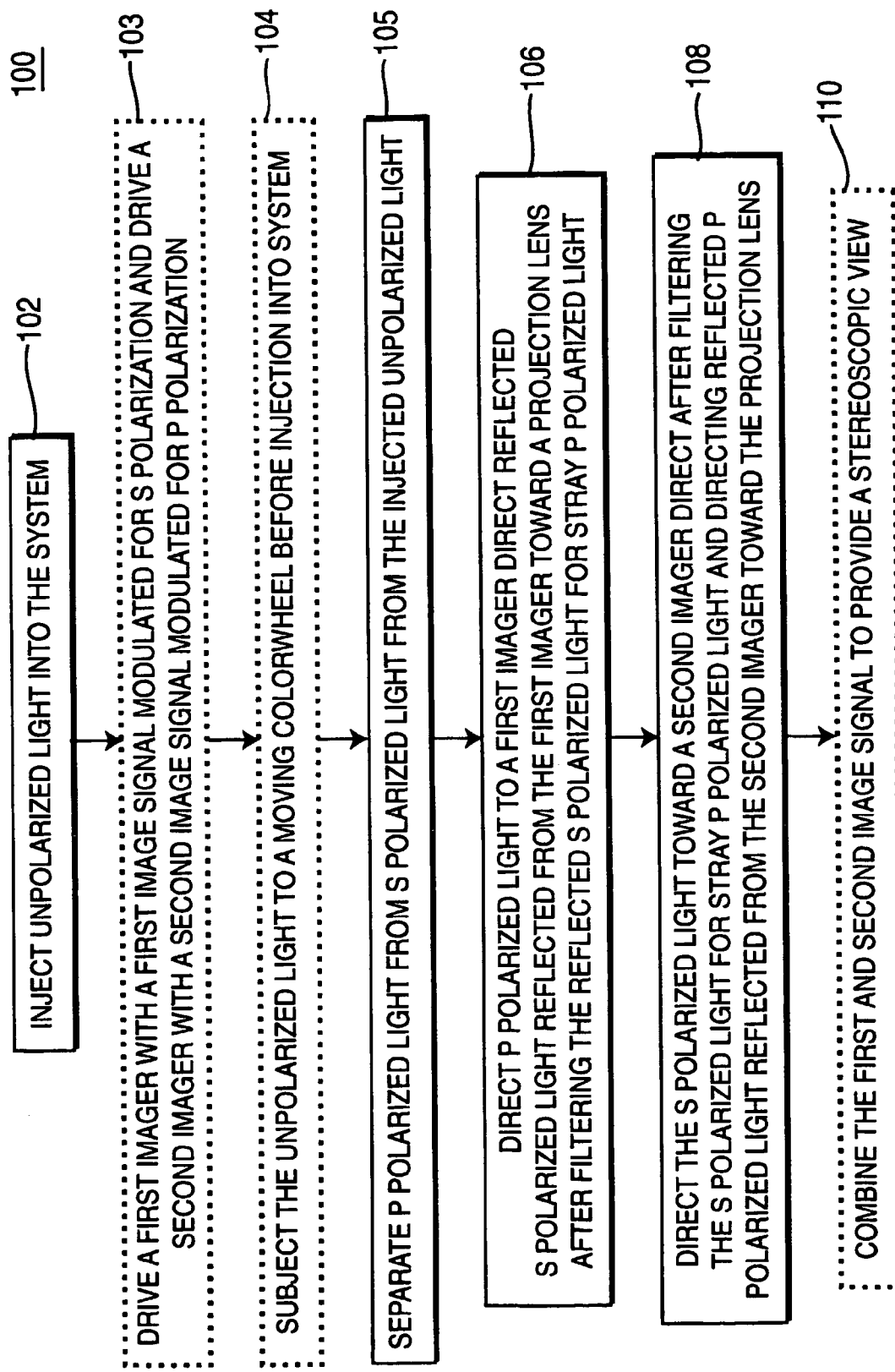
FIG. 3 is a flow chart illustrating a method of increasing brightness in a light engine and optionally being able to view images stereoscopically in accordance with the present invention.

Referring to FIG. 3, a flow chart illustrating a method 100 of increasing brightness in a liquid crystal display projection system is shown. At step 102, unpolarized light is injected into the system. Optionally, at step 103, the first imager and the second imager could be driven with different signals to produce polarization based stereo vision. As another option at step 104, the unpolarized light could be subjected to a rotating color wheel before injecting the unpolarized light into the system. Then, P polarized light is separated from S polarized light from the injected unpolarized light at step 105. At step 106, the P polarized light is directed to a first imager and reflected S polarized light reflected from the first imager is directed toward a projection lens after filtering the reflected S polarized light for stray P polarized light. As previously shown in FIG. 2, the dashed arrows illustrate the stray P polarized light. At step 108, the S polarized light is directed toward a second imager after filtering the S polarized light for stray P polarized light and directing reflected P polarized light reflected from the second imager toward the projection lens. At this point, light reflected from the first and second imagers can be combined at step 110. If the images were modulated appropriately, the first and second images can be combined to provide a stereoscopic image using polarization.

Figure 4:
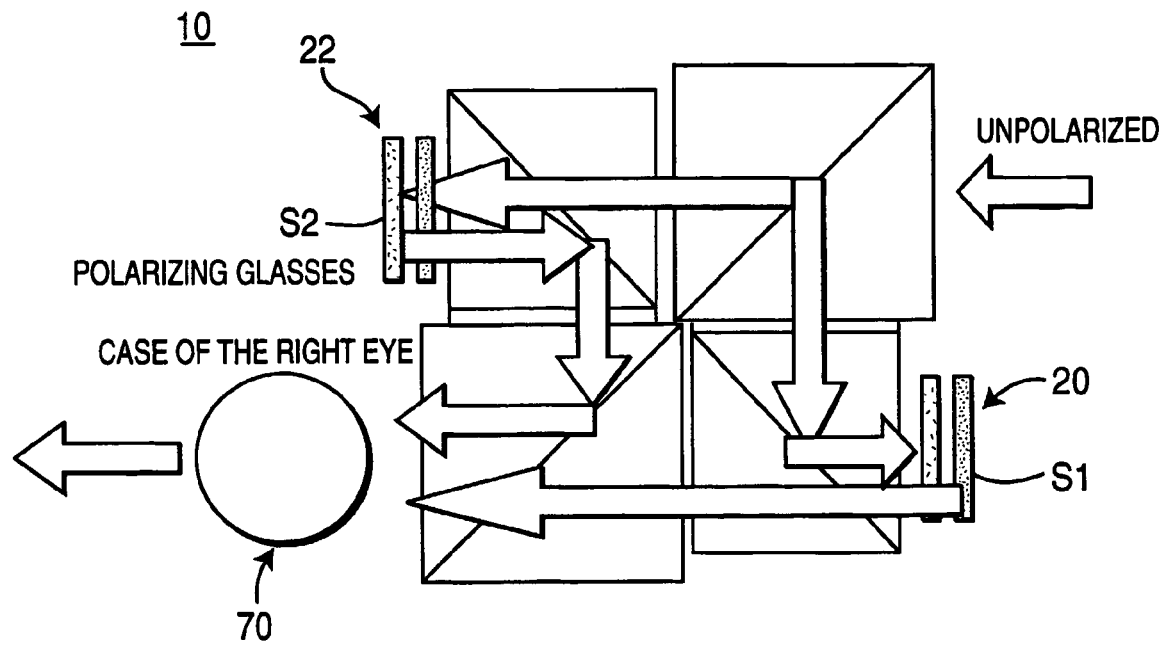
FIG. 4 is a block diagram of the light engine architecture of FIG. 1 displaying information corresponding to a right eye image with a first imager in accordance with the present invention.
Figure 5:
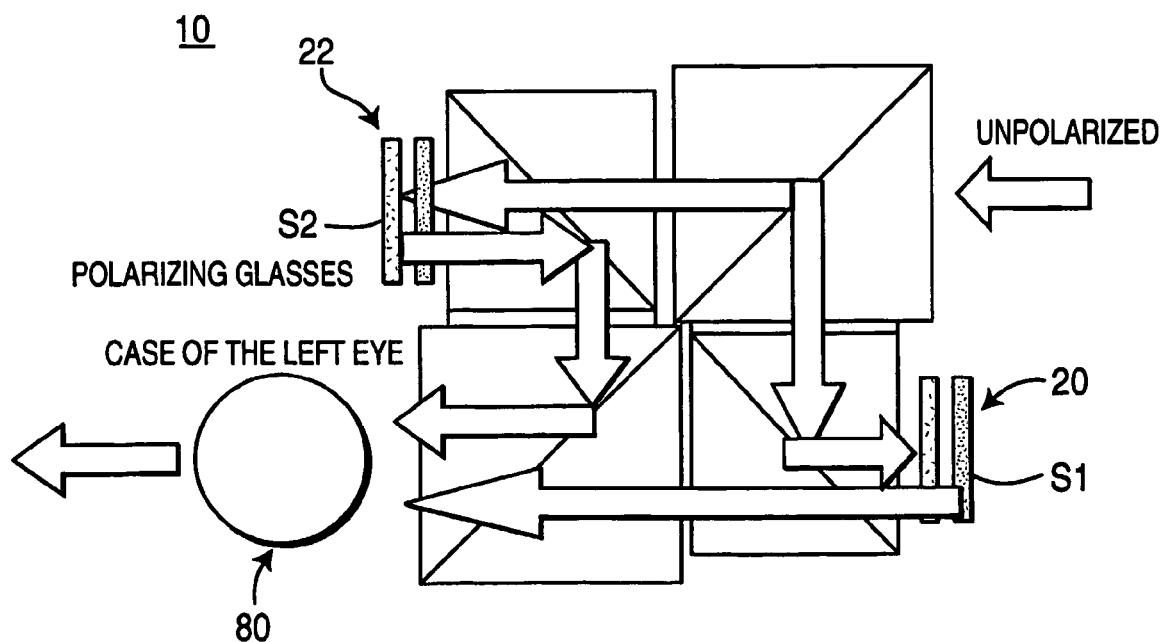
FIG. 5 is a block diagram of the light engine architecture of FIG. 1 displaying information corresponding to a left eye image with a second imager in accordance with the present invention.

Referring to FIGS. 4 and 5, the first imager 22 displays information corresponding to a first image intended for a right eye of a viewer. The second imager 20 displays information corresponding to a second image intended for a left eye of a viewer. This arrangement results in S polarized light directed to the right eye and P polarized light directed to the left eye. To filter any unwanted P polarized light that would go to the right eye of the viewer or any unwanted S polarized light going to the left eye of the viewer, the viewer would wear polarized glasses. The polarized glasses would have a polarizer 70 oriented so that only S polarized light would reach the right eye and another polarizer 80 oriented so that only P polarized light would reach the left eye. Of course, it should be understood within contemplation of the present invention that stereoscopic images could equally be generated and viewed by reversing the corresponding polarizations and images as needed.

It should be understood that the present invention could described in a myriad of different other arrangements within the scope of the claims or that other imagers could be used other than LCOS microdisplays as described herein. Although the present invention has been described in conjunction with the embodiments disclosed herein, it should be understood that the foregoing description is intended to illustrate and not limit the scope of the invention as defined by the claims.

The invention claimed is:

1. A liquid crystal display projection system for pictures that can be viewed stereoscopically, comprising:
    means for supplying a repetitive three color sequence of light;
    first and second imagers responsive to respective drive signals representative of the same picture from different angles of view;
    at least a first polarizing beam splitter for separating said repetitive three-color sequence of light into a P polarized three color sequence of light and an S polarized three color sequence of light, said S polarized three color sequence of light illuminating said first imager and said P polarized three color sequence of light illuminating said second imager;
    a first filter for removing P polarized light directed to said first imager; and,
    a second filter for removing P polarized light reflected from said second imager,
    wherein said light reflected from said first imager and said light filtered by said second filter form a stereoscopic image when viewed through respective P and S polarizing lenses;
    wherein the at least first polarizing beam splitter comprises four polarizing beam splitters including the first polarizing beam splitter, a second polarizing beam splitter for directing S polarized light split from the first polarizing beam splitter toward the second imager, a third polarizing beam splitter for directing S polarized light reflected from the first imager towards a fourth polarizing beam splitter, wherein the fourth polarizing beam splitter directs S polarized light reflected from the first imager and P polarized light from the second imager towards the projection lens; and
    wherein the system further comprises a first quarter wave plate between the third polarizing beam splitter and the first imager and a second quarter wave plate between the second polarizing beam splitter and the second imager.

2. The system of claim 1, wherein the first imager and the second imager are liquid crystal on silicon display devices.

3. The system of claim 1, comprising only said first and second imagers.

4. The system of claim 3, wherein the system further comprises a color wheel placed between at least the first polarizing beam splitter and the source of unpolarized light.

5. The system of claim 1, wherein the system further comprises a projection lens.

6. The system of claim 5, wherein the at least first polarizing beam splitter comprises a wire grid polarizer.

7. The system of claim 1, wherein the liquid crystal display projection system further comprises a pair of polarizing glasses worn by a viewer of the device wherein the polarizing glasses has a right lens polarizer oriented to allow only S polarized light through and a left lens polarizer oriented to allow only P polarized light through.

8. The system of claim 7, wherein the S polarized light passing through the right lens polarizer corresponds to the right image and the P polarized light passing through the left lens polarizer corresponds to the left image.

* * * * *